United States Patent [19]

Driker

[11] 4,324,130

[45] * Apr. 13, 1982

[54] METHOD AND APPARATUS FOR MEASURING THE MELTING TEMPERATURE OF GREASY PRODUCTS

[76] Inventor: Benjamin Driker, 35-04 21 Ave., Astoria, New York, N.Y. 11105

[*] Notice: The portion of the term of this patent subsequent to Apr. 13, 1996, has been disclaimed.

[21] Appl. No.: 717,541

[22] Filed: Aug. 25, 1976

[51] Int. Cl.³ .......................................... G01N 25/04
[52] U.S. Cl. .................................................. 73/17 R
[58] Field of Search ........................................ 73/17 R

[56] References Cited

U.S. PATENT DOCUMENTS

| | | | |
|---|---|---|---|
| 1,096,911 | 5/1914 | Hawxhurst | 73/17 |
| 3,173,288 | 3/1965 | Davis et al. | 73/17 |

Primary Examiner—Herbert Goldstein

[57] ABSTRACT

A method and apparatus for measuring the melting temperature of greasy products in a liquid flow wherein two samples streams are continuously draining from the flow, one of the streams, being frozen into a snow-like state, is fed into a perforated vessel floating inside a container fed by the second stream which mixes with and melts the first stream and overflows from the container.

The weight of the mixture fluctuates with changes of melting temperature and so does its depth in the second stream.

The change of the depth changes the temperature of the mixture.

The measured continuously and monitors temperature of the mixture is a regulating device.

7 Claims, 2 Drawing Figures

METHOD AND APPARATUS FOR MEASURING THE MELTING TEMPERATURE OF GREASY PRODUCTS

BACKGROUND OF THE INVENTION

The present invention relates to the method and apparatus of measuring the melting temperature of greasy products in a liquid flow of these products.

Production of many greasy products for food or for industrial consumers requires continuous control of melting temperature of these products or of semi-products composing a product. This temperature is a guaranteed parameter of such products.

There are in the prior art methods and apparatuses for this measuring which are using a discrete mode of measurement. The following is an example of measuring cycle in the prior art:

draining a liquid probe of product in the measuring vessel until the vessel is filled, cooling the probe in the vessel to the solid state, heating the probe in the vessel until the appearance of the first drop of liquid from the hole in the vessel's bottom, measuring and recording a temperature inside the vessel in the very instant of this drop, discharging the probe and shift to the next cycle.

This cyclic operation requires a lot of controls that causes a low reliability and high cost.

The melting temperature is not controlled in the time interval between the cycles that makes a quality of such measurement not a high one.

SUMMARY OF THE INVENTION

One object of the present invention is a method of measuring continuously the melting temperature of greasy products in a liquid flow of these products.

A second object of the invention is a simple, reliable and inexpensive apparatus for this method of measuring.

A third object of the invention is a combination of measuring and regulating means for correlating the value of product parameters in accordance with the fluctuating value of product melting temperature.

In accordance with the invention method there are two liquid streams draining continuously from the flow of product. One of the streams is freezing to a snow-like state and dipping in the second liquid stream. Thereby a flowing melting mixture is establishing with a heat transferring from the liquid stream for melting the frozen stream. The dipping of the frozen stream into the liquid stream is changing in accordance with fluctuations of the melting temperature. This causes corresponding correlation of the quantity of the transferring heat and of the temperature of melting mixture. The temperature of this changing depth melting mixture is measured continuously.

In the invention apparatus these two streams are draining by two pipes. A cooling device feeding from one of two pipes freezes one of two streams to a snow-like state. A floating vessel with holed walls is feeding from the cooling device by the frozen stream. A container containing this floating vessel is feeding by the second of two streams from second of two pipes. The second stream carries the floating vessel in a partially dipped floating state, mixes with the frozen stream, melts it and overflows with the melted stream from the container. A device for measuring continuously a temperature of the melting mixture has an operatively connected temperature sensor which is located and fixed in the floating vessel. The device for measuring a temperature produces output signals corresponding to the measured values of temperature of the mixture. A regulating device receives these signals and correlates the value of parameters of the product in accordance with the fluctuating value of the signals.

The floating vessel has a float and fixed to it.

The container contains an inner holed wall surrounding the floating vessel for smoothing perturbations in the second liquid stream.

The cooling device has a rotating screw located inside the cooled tube. This tube is located inside another tube forming a passage for a cooling agent flow. The screw conveys the one liquid stream during the process of freezing the stream and shaves frozen particles from the inner surface of the cooled tube, providing the snow-like frozen stream. The drive fixed on the cooling device rotates the screw.

The above mentioned and other objects and features of the invention will be more fully understood when read in conjunction with the drawing.

DESCRIPTION OF THE PREFERRED EMBODIMENTS

Figure 1:
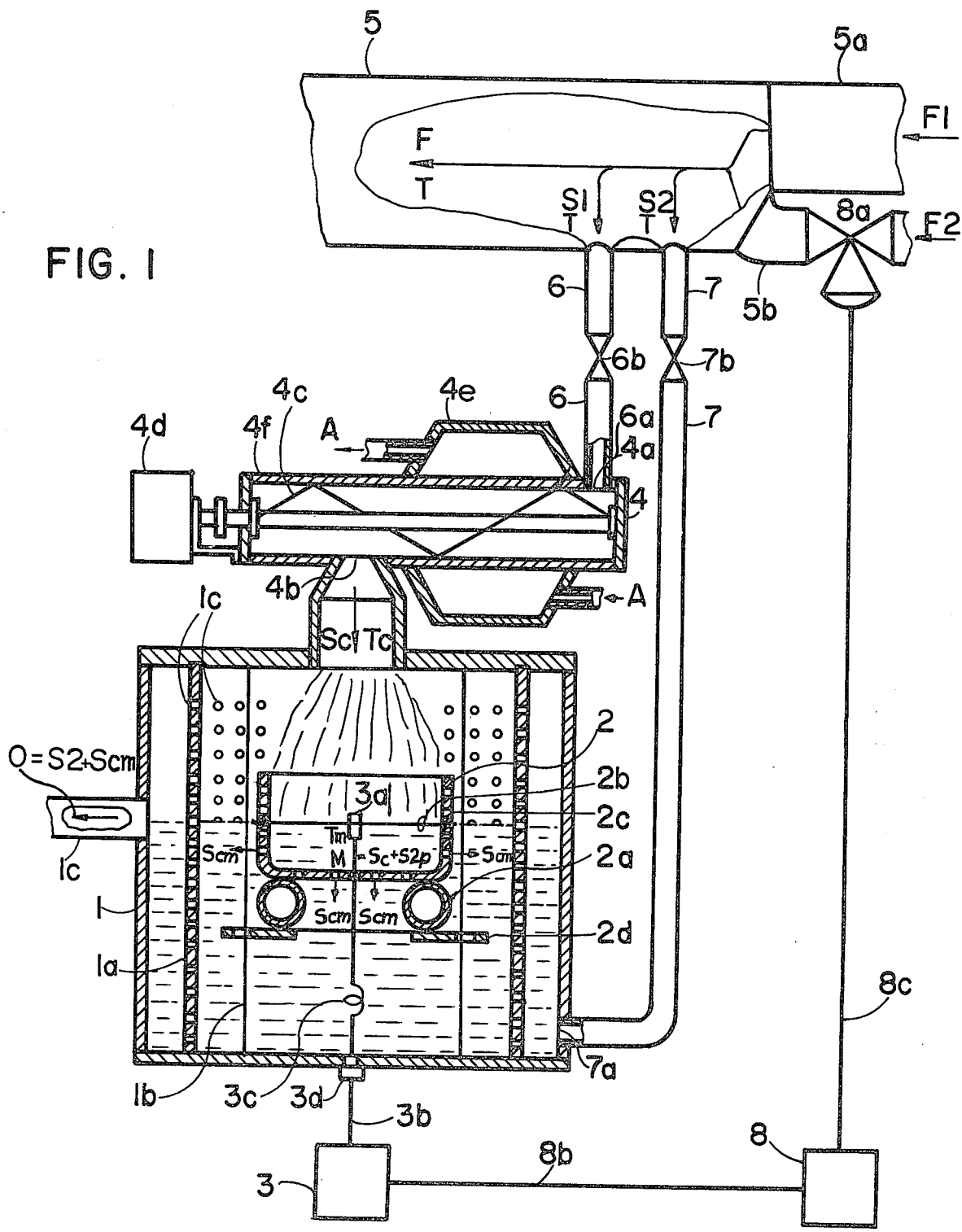
FIG. 1 is a diagramatic view on the invention.

FIG. 1 illustrates:

A liquid flow F of greasy product which melting temperature Tm is measured; the flow F is flowing in a pipe 5.

A pipe 6 and a pipe 7 draining the streams S1 and S2 respectively from the flow F.

The flow F and both of the streams have a temperature T.

A cooling device 4 receiving in the inlet 4a liquid stream S1 through the outlet 6a of the pipe 6 freezes this stream to a snow-like state stream Sc with a temperature Tc.

A floating vessel 2 with walls having holes 2c receives stream Sc from the outlet 4b of the cooling device 4.

A container 1 containing the floating vessel 2 receives stream S2 through the outlet 7a of the pipe 7.

The stream S2 carries the vessel 2 in a partially dipped floating state, mixes itself with stream Sc, melts stream Sc transferring it in the melted stream Scm, and overflows with stream Scm in the overflow $O=S2+Scm$ through the pipe 1c from container 1.

A device 3 for measuring continuously a temperature Tm of the melting mixture $M=Sc+S2p$. $S2p$ is a portion of stream S2 which is in a mixture with stream Sc in the vessel 2. The device 3 is operatively connected with its temperature sensor 3a by cable 3b and flexible cable 3c through fitting 3d. The sensor 3a is suspended inside the vessel 2 by tension wire 2b. The device 3 produces output signals corresponding to the measured values of the melting mixture M temperature.

A regulating device 8 operatively connected to the device 3 by cable 8b. The device 8 arranged to correlate the value of parameters of the product in accordance with the fluctuating value of the output signals from device 3. In the example shown on FIG. 1 device 8 operates valve 8a through cable 8c. Valve 8a changes its opening in accordance with commands obtaining from device 8. Thereby the quantity of component flow F2 entering the inlet 5b of the pipe 5 is changing correspondingly. The flow F in this example is a mixture of F2 and another component flow F1 entering the inlet 5a of the pipe 5. So, correlation of quantity between components is changing, that causes changes of value of parameters of product flow F.

The floating vessel 2 has a float 2a and fixed to it.

The container 1 has an inner wall 1a with holes 1c; this wall surrounds the vessel for smoothing perturbations in the stream S2.

Rods 1b and rings 2d fixed to the container 1 and floating vessel 2 respectively are for holding this vessel in a proper vertical direction.

The cooling device 4 has an outer tube 4e and concentric inner tube 4f. The space between the tubes is for passing a cooling agent A. The drive 4d fixed on the cooling device 4 rotates the screw 4c located inside the inner tube 4f.

When liquid stream S1 enters the inner tube 4f, screw 4c sprinkles this liquid on the freezing surface of the tube and then shaves frozen particles from this surface, providing and conveying snow-like stream Sc to the outlet 4b that is unloading by gravity.

Set-point correlation between expenditures in the S1 and S2 streams is provided for particular product by proper openings of valves 6b and 7b.

Thus it can be observed:

First: The melting mixture's depth is changing and correlating its measuring temperature correspondingly to fluctuations of the melting temperature of product.

Second: The melting mixture's depth is changing and compensating its measuring temperature from interferences correspondingly to fluctuations of the temperature in the flow of product.

Third: Depth changing responses in the above two events have opposite directions.

Figure 2:
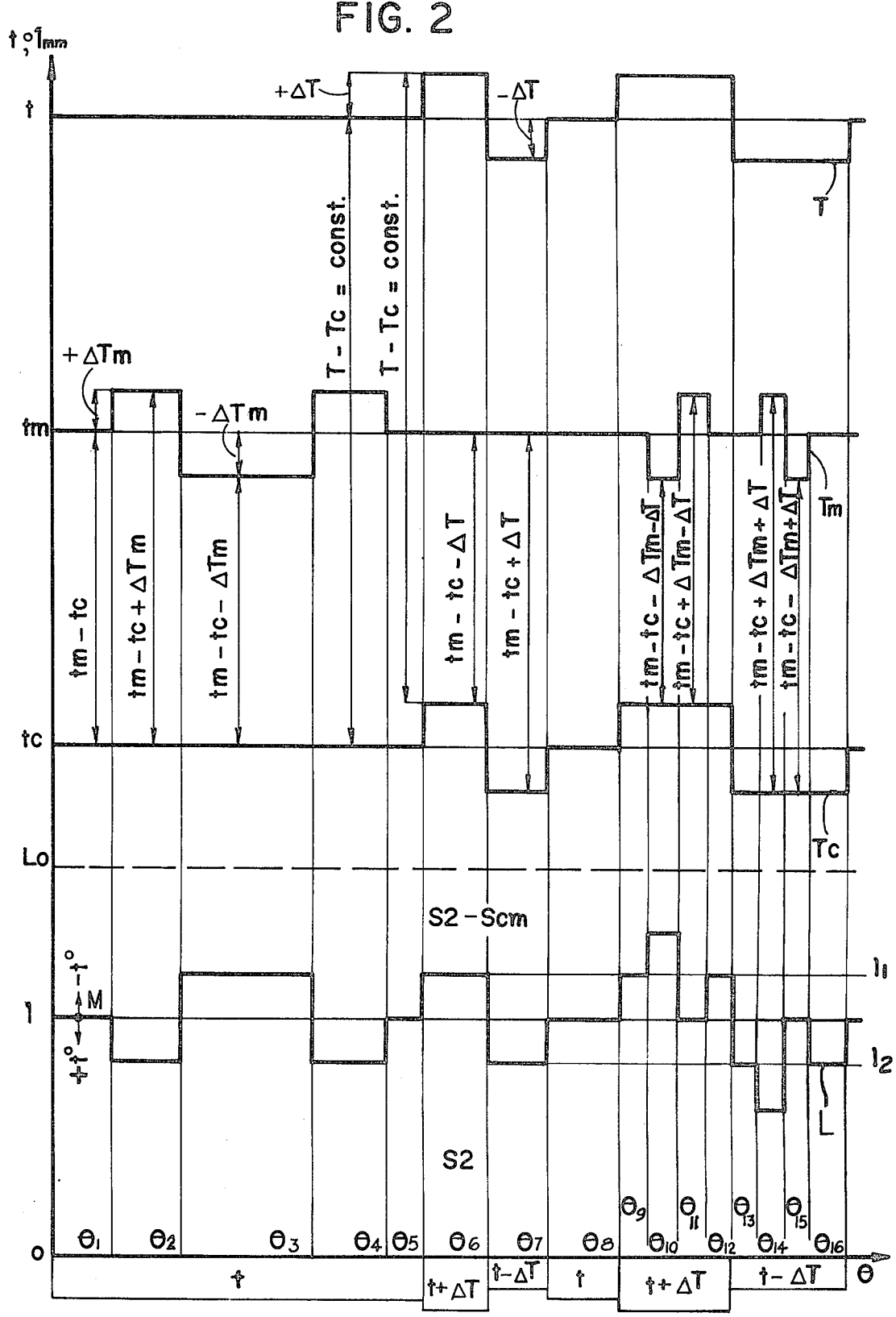
FIG. 2 is an example of chart showing dependence of dipping of the melting mixture from fluctuations of measuring melting temperature and of flow temperature.

FIG. 2 is an example that shows graphs of melting temperature Tm, temperatures T and Tc of streams S2 and Sc respectively and of level L of dipping mixture M in the stream S2, during the time $\theta$ measured along abscissa. Mixture M shown as a current point on the graph of L. Temperature t° and level lmm are measured along ordinate. The t, tm, tc, and l are representing the average values of T, Tm, Tc and L respectively. Lo represents the level of overflow from container 1; the area below the dotted line of Lo represents liquid streams—S2 below the graph L and S2+Scm above this graph. Rectangles below absciss are another designation of value of the temperature T of stream S2.

For simplification of FIG. 2, delays between causes and responses are not shown; all changes are shown as instantaneous changes; all values of the changes shown in equal ordinate dimensions.

Further, the description considers that expenditures of product by the streams Sc and S2 during the current time are steady, and the total amount of heat taken off from the stream S1 in the cooling device during the current time is also steady. Or it can be considered that T−Tc=constant, as shown on FIG. 2.

The above consideration is a practical one and does not require special provision in application.

The partial amount of heat Qc taken off from the stream S1 below the melting temperature Tm in the cooling device during the current time is determined by the difference Tm−Tc.

The amount of heat Qcm, consuming from stream S2 by stream Sc during the current time for melting stream Sc is determined by the level L. The Qcm increases when the L decreases and vice versa because the deeper the mixture M the more particles from both streams become interacting and vice versa. Thereby the temperature of this mixture M increases when the L decreases and vice versa. This is shown on FIG. 2 by the vertical arrows −t° and +t° at the point of M.

When Qc and Qcm are equal, entering and melting loading on vessel 2 from stream Sc are equal also Sc=Scm, and vessel 2 stays on a level corresponding to these equalities, balances of heat and load.

Therefore, the changes of Qc demand changed Qcm which can be consumed only on the changed level; this changed level is obtaining automaticly because Sc demands changed Scm also and moves vessel 2 up or down until reestablishing of the heat and load balances. For example, if Qc is smaller than Qcm, Sc become smaller than Scm also, therefore vessel 2 emerges to the level where Qcm and Scm are decreasing to the equalities with Qc and Sc respectively, and vice versa.

There are two causes of changing Qc:

$\Delta$Tm—the changes of melting temperature Tm, and-
/or
$\Delta$T—the changes of temperature T.

FIG. 2 shows three events following these causes:

Tm=variable, T=constant—instants $\theta$1 through $\theta$4
Tm=constant, T=variable—instants $\theta$5, $\theta$6 and $\theta$7
Tm=variable, T=variable—instants $\theta$8 through $\theta$16

For the first event: When T=t and Tm=tm, $Tm-Tc=tm-tc$ and L=1; When Tm changes to $Tm=tm+\Delta Tm$, $Tm-Tc=tm-tc+\Delta Tm$ this corresponds to the increase of Qc that can be compensated by the equal increase of Qcm which can be consumed only on a deeper than 1 level L, as shown in the time intervals $\theta$1 to $\theta$2 and $\theta$3 to $\theta$4. Vice versa example for the first event is similar and shown in the time interval $\theta$2 to $\theta$3.

For the second event: When $T=t+\Delta T$, $Tm-Tc=tm-tc-\Delta T$ this corresponds to the decrease of Qc that can be compensated by the equal decrease of Qcm which can be consumed only on a shallower than 1 level L, as shown in the time interval $\theta$5 to $\theta$6. Vice versa example for the second event is similar and shown in the time interval $\theta$6 to $\theta$7.

For the third event: When $Tm=tm-\Delta Tm$ and $T=t+\Delta T$, $Tm-Tc=tm-tc-\Delta Tm-\Delta T$. Now two components are causing the decrease of Qc bigger than was before and corresponding decrease of Qcm can be consumed on a shallower than before level L, as shown in the time interval $\theta$9 to $\theta$10.

In the time interval $\theta$10 to $\theta$11 Tm changes to $Tm=tm+\Delta Tm$ and now $Tm-Tc=Tm-tc+\Delta Tm-\Delta T$, therefore the Qc is causing to increase by one and to decrease by another of components and in accordance with our scale level L takes value 1.

Similar explanations can be made for $Tm-Tc=tm-tc+\Delta Tm+\Delta T$ in the time interval $\theta$13 to $\theta$14 and for $Tm-Tc=tm-tc-\Delta Tm+\Delta T$ in the time interval $\theta$14 to $\theta$15.

In conclusion of these events description we can see that the average value t of temperature T determines the average value l of level L, the initial level arround which the mixture M is moving when melting temperature Tm is fluctuating.

When T is changing, L is changing also and mixture M is now moving arround new initial level on which the temperature of this mixture is compensated from the changes caused by changed T.

As FIG. 2 shows, in the time interval 0 to $\theta 5$ T=t that corresponds to the initial level l, arround which the mixture M moves in response on fluctuations of Tm.

In the time interval $\theta 5$ to $\theta 6$ T=t+$\Delta$T and mixture M changes its initial level to the shallower value l1. For the time interval $\theta 6$ to $\theta 7$ T=t−$\Delta$T and the initial level has a dipper value l2.

In the time intervals $\theta 9$ to $\theta 11$ and $\theta 13$ to $\theta 15$ we see mixture M moving arround these shallower and dipper initial levels respectively in response on fluctuations of Tm.

Now we can say that combined responses of L on fluctuations of Tm and T are directed for keeping the temperature of the melting mixture M correlated by Tm only, or for keeping this temperature of melting mixture equal to the values of Tm with a good accuracy.

The gist of the present invention desired to be protected by Letters Patent is set forth in the appended claims.

I claim:

1. A method of measuring the melting temperature of greasy products in a liquid flow thereof comprising:
   forming a continuous flow of first and second liquid streams from said product;
   freezing said first stream to a snow-like state;
   feeding said second liquid stream to a container;
   feeding said snow-like material into a vessel having perforated walls, said vessel resiliently supported in the liquid in said container, whereby the liquid in said container passes through the vessel walls to mix with and melt the snow-like material, and the depth of the vessel in said liquid changes in response to changes in mixture weight which in turn changes with variations of melting temperature; and,
   continuously measuring the temperature of material in the vessel.

2. An apparatus for measuring the melting temperature of greasy products in a liquid flow thereof comprising:
   two pipes continuously draining a first and a second liquid stream from said flow;
   a cooling device connected to one of said pipes to receive the first stream and to freeze said first stream to a snow-like state;
   a floating vessel having perforated walls and receiving said snow-like material from an outlet of said cooling device;
   a container, including overflow means, containing said floating vessel, said container connected to the other of said pipes to receive the second liquid stream which carries said vessel afloat so that the lower portion of the vessel's perforated walls is beneath the liquid surface, the second stream passing through said vessel walls to mix with and melt the snow-like material in said vessel, said mixture overflowing from said container; and,
   a device for continuously measuring the temperature of the mixture in said vessel.

3. An apparatus as defined in claim 2 wherein;
   said device for measuring a temperature having an operatively connected temperature sensor, the sensor being located in said floating vessel and fixedly attached thereto.

4. An apparatus as defined in claim 2 wherein;
   said device for measuring a temperature produces output signals corresponding to the measuring values of temperature of said mixture and further comprising,
   a regulating device operatively connected to said device for measuring a temperature and arranged to modify the value of parameters of said product in accordance with the fluctuating value of said output signals.

5. An apparatus as defined in claim 2 further comprising;
   a float fixedly connected to said floating vessel.

6. An apparatus as defined in claim 2 wherein;
   said container having an inner perforated wall surrounding said floating vessel for smoothing perturbations in said second stream.

7. An apparatus as defined in claim 2 wherein;
   said cooling device comprising,
   two concentric tubes, the outer of the tubes being arranged for passing a cooling agent in the space between tubes, the inner of the tubes having two ends, one of the ends is the inlet and second of the ends is the outlet of said cooling device;
   a rotable screw in the inner tube for transforming to a snow-like state and conveying of said one stream from the inlet to the outlet during the process of freezing the stream;
   a drive fixed on the cooling device for rotating the screw.

* * * * *